United States Patent [19]

Annis

[11] 4,260,898

[45] Apr. 7, 1981

[54] X-RAY IMAGING VARIABLE RESOLUTION

[75] Inventor: Martin Annis, Newton, Mass.

[73] Assignee: American Science and Engineering, Inc., Cambridge, Mass.

[21] Appl. No.: 946,913

[22] Filed: Sep. 28, 1978

Related U.S. Application Data

[63] Continuation of Ser. No. 782,973, Mar. 30, 1977, abandoned.

[51] Int. Cl.² ............................................. G03B 41/16
[52] U.S. Cl. .............................. 250/505; 250/416 TV; 250/511
[58] Field of Search ........ 250/505, 511, 512, 416 TV, 250/358 R; 358/111

[56] References Cited

U.S. PATENT DOCUMENTS

| | | | |
|---|---|---|---|
| 3,894,234 | 7/1975 | Mauch | 250/416 TV |
| 4,031,401 | 6/1977 | Jacob | 250/514 |

*Primary Examiner*—Craig E. Church

*Attorney, Agent, or Firm*—Pollock, Vande Sande & Priddy

[57] ABSTRACT

A scanning X-ray imaging system produces an image of the transmissivity of objects by producing a relative motion of the object generally perpendicular to the triangular planes joining an X-ray point source and M X-rays pass through a scanning slit assembly. The scanning slit assembly generally includes a plane of X-ray opaque material having N sets of line slits, where N is equal to or greater than 2, each set containing MM identical line slits. The scanning slit assembly, in addition, includes a rotating X-ray opaque material containing N uniquely different sets of slits, each set containing identical slits. Each of the N sets of slits is uniquely paired with each of the M . N line slits. During any scan of an object, M detectors, M line slits and one of the N sets of slits are used. The scanning X-ray imaging system provides N selections in image resolution of the scanned object. The selectivity provides radiographic images with different contrast resolution and/or spatial resolution.

22 Claims, 6 Drawing Figures

X-RAY IMAGING VARIABLE RESOLUTION

This is a continuation of application Ser. No. 782,973, filed Mar. 30, 1977, now abandoned.

BACKGROUND OF THE INVENTION

The present invention relates in general to penetrating radiant energy imaging and more particularly concerns novel apparatus and techniques for selectively obtaining X-ray images of variable density contrast and/or spatial resolution with a modification of commercially available MICRO-DOSE X-ray apparatus disclosed in U.S. Pat. No. 3,780,291, manufactured and sold by American Science & Engineering, Inc. The invention readily achieves magnification and greater resolution in the image of a scanned object with an improved scanning slit assembly.

The present invention represents an improvement of the invention in U.S. Pat. No. 3,780,291, embodied in the commercially available AS&E MICRO-DOSE X-ray imaging system used in airports and other locations for parcel inspection. In that system a moving pencil beam of X-rays repeatedly scans a line detector as the scanned object is translated past the beam and detector assembly. The line detector produces light signals representative of the incident X-ray energy, which are then converted by photoelectric detecting means to video signals representative of the X-ray transmissivity between the beam source and the detector. From the video signals, a video system displays a sequence of horizontal lines to provide a two dimensional image of the scanned object.

Four radial slits in a rotating disc of X-ray opaque material successively intercept the line beam to produce a pencil beam that scans the length of the line detector as the radial slits rotate; the intersection of one of the four slits and their corresponding line slit moves from one end of the line beam cross section to the other.

It is an important object of this invention to provide an improved X-ray imaging system.

It is another object of the invention to achieve the preceding object with a system that provides increased density contrast as a trade-off against the size of the area of the object being imaged.

It is still another object of the invention to provide an improved X-ray imaging system that provides increased density contrast without decreasing the area of the object being imaged by increasing the number of detectors.

It is a further object of the invention to achieve one or more of the preceeding objects with relatively slight modification of the prior art system described above.

It is still a further object of the invention to achieve one or more of the preceding objects by selectively displacing the relative position between the scanning slit assembly and the detector and X-ray source.

It is still a further object of the invention to achieve one or more of the preceding objects economically and with high reliability while permitting a relatively unskilled operator to easily effect the change in resolution/contrast.

It is still a further object of the invention to utilize essentially the same logic electronics for each of the images constructed using any of the line slit-radial slit combinations.

It is still a further object of the invention to have a fixed spatial relationship between the images formed by each line slit-radial slit combination, allowing a small area of one of the larger images to be easily X-rayed at higher density and/or spatial resolution.

SUMMARY OF THE INVENTION

According to one embodiment of the invention, there is a scanning X-ray imaging system with a line detector and a first X-ray opaque member having at least one slit with lengths aligned essentially along the length of the line detector and a second X-ray opaque member having at least first and second sets of radial slits for relative movement across the line cross section of the region bounded by the line detector and a said slit in the first member, said first and second sets being radially displaced relative to a common axis of rotation. The first and second members are relatively displaceable in a direction perpendicular to the line cross section between first and second positions with the first and second sets of slits, respectively, capable of intercepting the line cross section to provide first and second magnification, spatial resolution, and density contrast, respectively. In a particular form of the invention there are four outer radial slits and twelve inner radial slits. In the former case, a larger area of the target is scanned four times per revolution and, in the latter, a smaller area is scanned twelve times per revolution. The smaller area receives a greater X-ray dose than the larger area which produces an improved density contrast and/or spatial resolution and image magnification.

Numerous other features, objects and advantages of the invention will become apparent from the following specification when read in connection with the accompanying drawing in which:

DETAILED DESCRIPTION OF PREFERRED EMBODIMENTS

Figure 1:
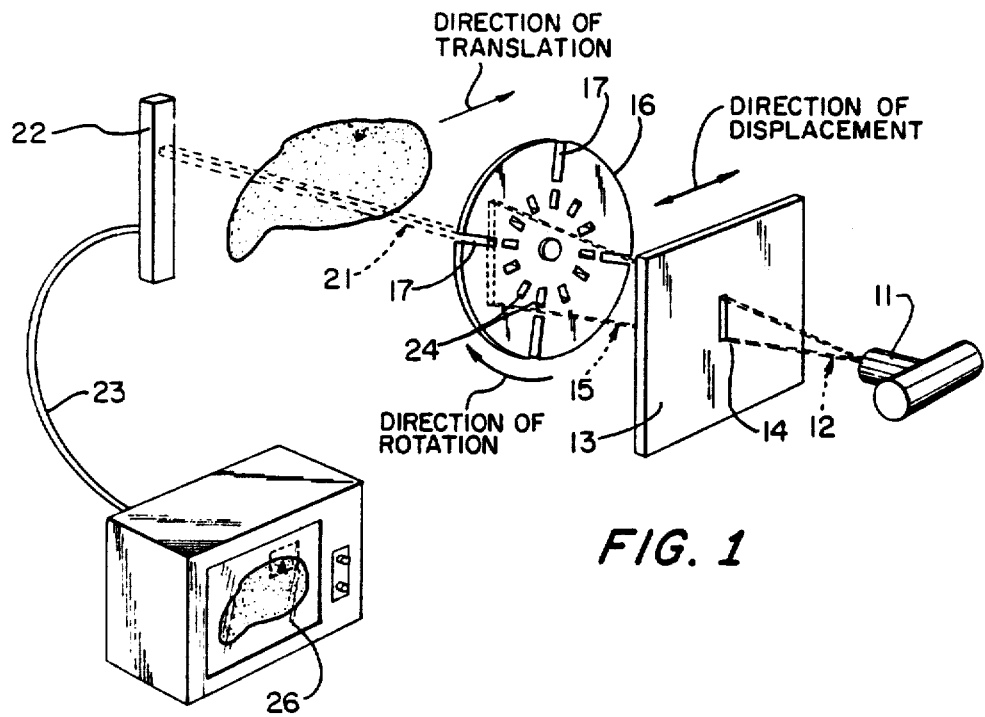
FIGS. 1 and 2 are diagrammatic representations of the scanning slit assembly and detector configuration according to the invention in respective ones of the two positions.

With reference now to the drawing and more particularly FIG. 1 thereof, there is shown a diagrammatic representation of the scanning slit assembly and detector configuration according to the invention. X-ray source 11 emits 9 cone shaped beam 12, which strikes a first member comprising an X-ray opaque plate 13. Line slit 14 in plate 13 collimates beam 12 into a linear beam 15, which strikes a second member comprising a rotating disc 16. Outer radial slits 17, spaced 90° apart, successively intersect linear beam 15 as disc 16 rotates to produce pencil beam 21 that repeatedly scans the length of a line detector 22 as the intersection of slits 17 and linear beam 15 moves from one end of linear beam 15 to the other. Only one radial slit 17 transmits beam 15 at each instant of time. Detector 22 produces a video signal on output line 23 representative of the X-ray response of the scanned object located in the region between disc 16 and detector 22. As the scanned object is relatively translated to the right, imaging means 26 produces a two dimensional image of the X-ray response of the scanned object in response to the sequence of video signals in a manner known in the art embodied in the commercially available AS&E ® MICRO-DOSE X-ray inspection system.

Figure 2:
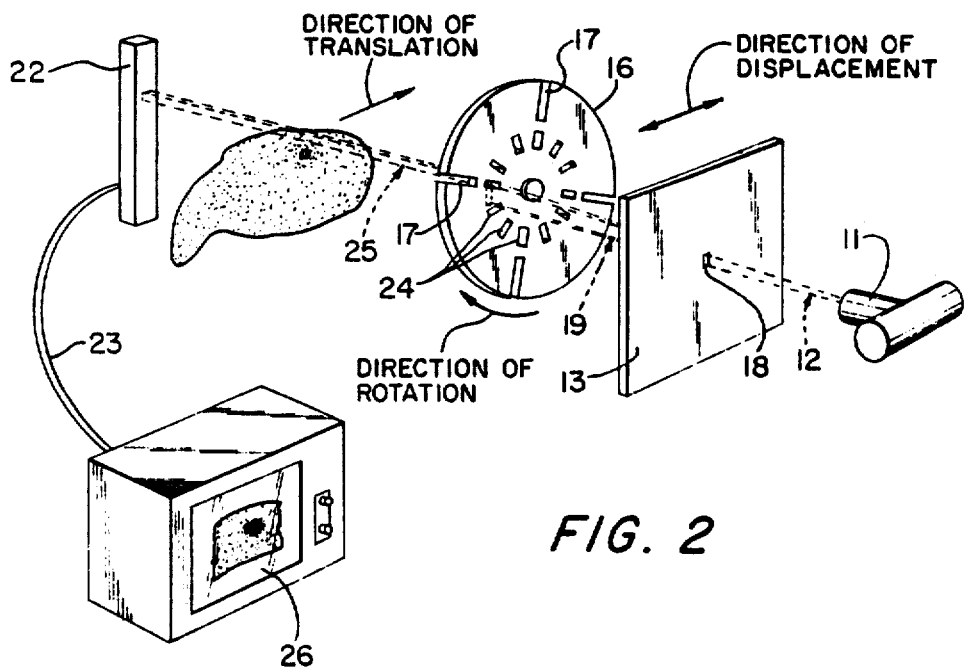

Referring now to FIG. 2 there is shown a diagrammatic representation of the configuration shown in FIG. 1 with disc 16 and plate 13 relatively displaced so that inner radial slits 24 intersect linear beam 19 collimated by slit 18, shorter than slit 14, for facilitating more detailed examination of a smaller area of interest. According to the invention, there are 12 additional radial slits 24 in disc 16, normally set narrower than each slit 17 and at a smaller radius. With disc 16 selectively displaced horizontally in its plane so that radial slits 24 successively intersect linear beam 19, pencil beam 25 of normally smaller cross section than that of beam 21 repeatedly scans a portion of line detector 22. Only one radial slit transmits X-rays at each instant of time.

Pencil beam 25 scans a smaller portion of the scanned object because the length of line slit 18 is smaller than that of line slit 14. Let $x_1$ be the ratio of the pencil beam 25 area to the smaller scanned area and $x_2$ be the ratio of the pencil beam 21 area to the larger scanned area. It is preferred that $x_1 > x_2$ and the total scanning time for both the smaller scanned area and the larger scanned area is the same. Thus the smaller area scanned by beam 25 receives $x_1/x_2$ more X-ray dose than the larger area scanned by beam 21. The result is an image with improved resolution and/or contrast, allowing image magnification of the smaller scanned area with increased resolution and contrast to facilitate detailed examination. The line slit 18 and radial slits 24, or line slit 14 and radial slits 17, may be adjustable in width to allow improved spatial resolution at the expense of contrast, or vice versa.

The specific embodiment described is to illustrate the principles of the invention. In a specific embodiment of the invention the chopper disc 16 is 18.8 inches in diameter and includes three sets of slits, each set located at a radius different from the radius of the other sets of slits. These three sets of radial slits and three corresponding line slits are each associated with a particular examination field size. The large field is approximately 15 inches wide by 20 inches long from scanning with four radial slits 17 spaced 90 degrees apart on the outer periphery of disc 16, each of radial length of 2.6 inches and adjustable width ≦0.08 inches, each passing over a line slit of length 11.5 inches, adjustable width ≦0.08 inches, and center located 6.0 inches from axis of wheel 16. The medium field is substantially 6 inches by 8 inches by scanning with six radial slits spaced 60 degrees apart each 0.69 inches in radial length and ≦0.06 inches adjustable width, each passing over a line slit of length 4.0 inches, adjustable width ≦0.06 inches, and center located 3.9 inches from the axis of chopper disc 16. The small field is 1.5 inches by 2 inches from scanning with a set of twelve radial slits each of 0.25 inches radial length by ≦0.05 inches adjustable width and spaced 30 degrees apart, each passing over a line slit of length 1.19 inches, adjustable width ≦0.05 inches, and center located 2.8 inches from the axis of the chopper wheel 16. The line and radial slits which form each pair have adjustable width so that contrast may be increased at the expense of spatial resolution or vice versa. The particular means for selectively positioning the chopper disc 16 and the rest of the apparatus and for providing synchronizing signals is not a part of the invention and not described in detail here to avoid obscuring the principles of the invention. There is preferably a separate source of a synchronizing signal for each set of scanning openings in chopper disc 16 so that a synchronizing signal is provided substantially at the beginning of each scan. The specific techniques for providing these synchronizing signals is substantially the same as embodied in the commercially available MICRO-DOSE X-ray inspection systems of American Science & Engineering, Inc. that uses a single set of slits.

To achieve the translation motion for developing the second dimension of the image, either the object to be scanned may be moved transverse to the beam, or as in the embodiment utilized here, the entire X-ray system comprising source-slit assembly and detector is moved transverse to the object to be scanned.

Although different areas are scanned depending upon which set of slits generate the X-ray pencil beam, the television display area is the same so that using the small field provides to the observer a display of the smaller area of interest magnified ten times over that of the large field display.

The specific means for storing and displaying the video signals derived from the individual scans is also not a part of the invention and may comprise analog storage, such as a silicon storage tube, video disc and film with readout by a conventional television display having 1023 lines and capable of storing 60 levels of gray scale. Alternatively, digital storage may be used that may comprise a Data General Nova 3 computer using a magnetic disc system and a video image processor with magnetic tape and film functioning for permanent record and television readout displaying 480×640 picture elements and capable of storing a gray scale of $2^{12}$ levels.

While the exemplary embodiment disclosed herein includes a rotating disc formed with sets of like apertures with the sets radially displaced and means for selectively displacing the chopper disc 16 in a direction transverse to the plane of linear beam 15 or linear beam 19, it is within the principles of the invention to use other scanning techniques. For example, the scanner might comprise a chopper of a geometrical form other than a disc. An alternate to the disc chopper is the drum chopper generally of the type disclosed in Belgian Pat. No. 839519 granted Mar. 31, 1976, in which the rim contains the radial slits. An advantage of the drum chopper is that it may scan an object that has to remain against some physical boundary, such as the floor. Another advantage of the drum chopper is that the analog between each radial slit in the rim is always 90° with respect to the line slit. This feature is advantageous when used with a multiple detector scanner because more than one pencil beam can be generated in such a manner that the spatial alignment of the intersections of each pencil beam with its dedicated line detector remains fixed during each complete scan of the detectors, and the pencil beams are of substantially constant rectangular cross section during each scan. This fixed alignment allows a much more simplified summation technique for adding the intensities of each pencil beam that is transmitted through each point on the scanned object; for the disc chopper in FIG. 1, the angle between each radial slit 17 and line slit 14 varies from 45° through 90° to 135°; for the disc chopper in FIG. 2, the angle between each radial slit 24 and line slit 18 varies from 75° through 90° to 105°. The purpose of using the multiple detector scanner shown in FIGS. 3 and 4, instead of the single detector scanner as shown in FIGS. 1 and 2, is to increase density contrast.

Figure 3:
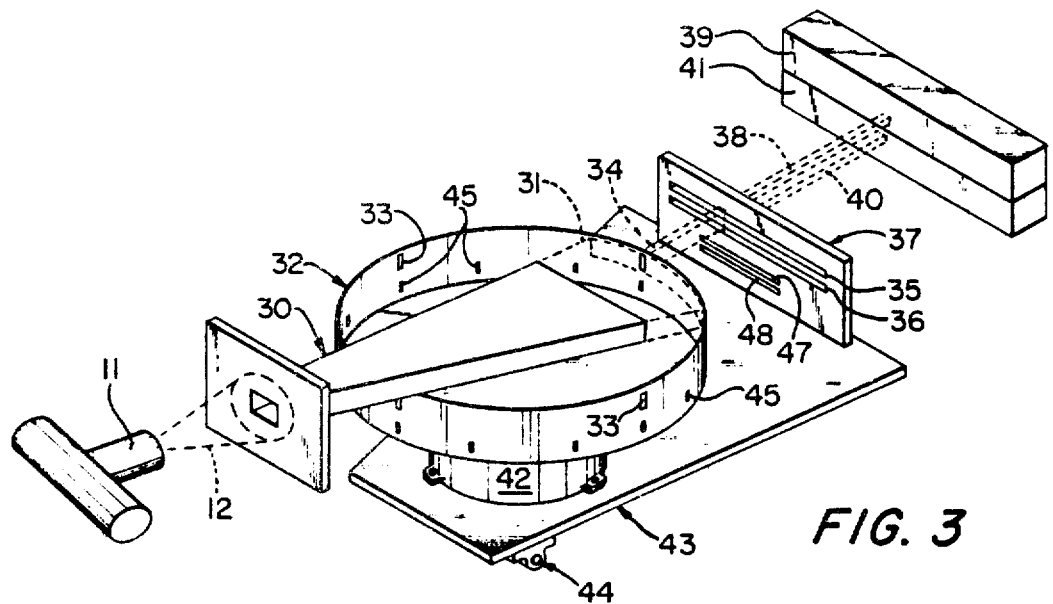
FIGS. 3 and 4 are diagrammatic representations of a scanning slit assembly and detector configuration according to the invention in respective ones of two positions in which multiple pencil beams simultaneously scan multiple detectors according to the invention.

With reference now to FIG. 3, there is shown a diagrammatic representation of the variable resolution drum chopper scanning slit assembly and multiple detector configuration according to the invention. X-ray source 11 emits a cone-shaped beam 12, part of which enters triangular-shaped X-ray collimator 30. The rectangular cross section of collimator 30 collimates beam 12 into a rectangular beam 31, which strikes the inside rim of rotating drum 32. The rim of X-ray opaque material contains the radial slits. Upper radial slits 33, spaced 90° apart, successively intersect rectangular beam 31 as drum chopper 32 rotates to produce slit beam 34 that repeatedly scans the length of line slits 35 and 36 located on X-ray opaque plate 37. Only one radial slit transmits X-rays at each instant of time. Line slit 35 collimates the upper part of slit beam 34 to produce pencil beam 38 that repeatedly scans the length of line detector 39; line slit 36 collimates the lower part of slit beam 34 to produce pencil beam 40 that repeatedly scans the length of line detector 41. The cross sections of pencil beams 38 and 40 are made equal to each other.

To easily convert the scanner in the large field mode as shown in FIG. 3 to the small field mode, the motor 42 for the drum chopper 32 and the X-ray opaque plate 37 are mounted on the supporting structure 43, which can rotate through a small angle about axis 44, which is perpendicular to the concentric axes of drum 32 and motor 42. As a result of the small rotation about axis 44, upper radial slits 33 pass above rectangular beam 31 and line slits 35 and 36 are above the plane containing the X-ray collimator 30 and rectangular beam 31.

Figure 4:
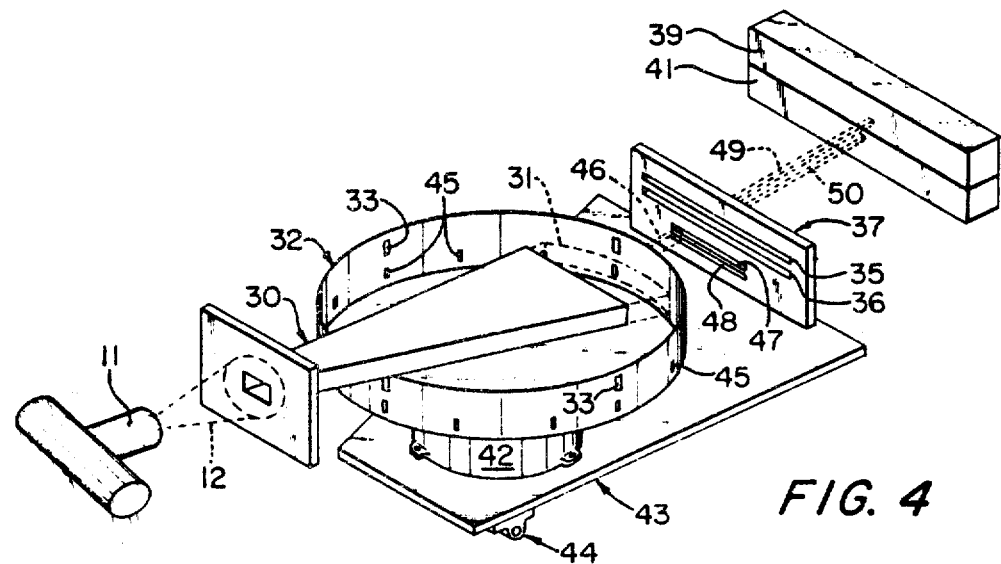

Referring now to FIG. 4, there is shown a diagrammatic representation of the configuratin shown in FIG. 3 but with drum 32 and plate 37 relatively rotated so that lower radial slits 45 intersect with rectangular beam 31 for facilitating more detailed examination in a small field mode. According to the invention, there can be 12 additional radial slits 45 in drum chopper 32, normally set narrower than each slit 33. With drum 32 selectively rotated so that radial slits 45 successively intersect rectangular beam 31 as drum 32 rotates to produce slit beam 46, slit beam 46 of normally narrower cross section than that of slit beam 34 repeatedly scans the length of line slits 47 and 48 located on plate 37. Line slit 47 collimates the upper part of slit beam 46 to produce pencil beam 49 that repeatedly scans the length of line detector 39; line slit 48 collimates the lower part of slit beam 46 to produce pencil beam 50 that repeatedly scans the length of line detector 41. Pencil beams 49 and 50 have equal cross sections and are normally set smaller than the cross sections of pencil beams 38 and 40. Only one pencil beam is generated for each detector at any instant of time.

If the object to be scanned moves down past line detectors 39 and 41, or the scanning system moves up past a stationary object to be scanned so that there is relative motion between the object and the scanner, the output signal provided by detector 39 is preferably digitized and stored in a linear array memory. When the second line detector 41, which provides an output signal that is also digitized at the same rate as for detector 39, corresponds to the same object's spatial transmissivity as represented by the data stored in a particular memory array, the spatially related digitized intensities are added together, converted to an analog video signal, and then transmitted over a video cable to an imaging means which produces a two-dimensional image of the X-ray response of the scanned object in a manner known in the art embodied in commercially available AS&E ® Micro-Dose ® X-Ray Inspection System. If a computer system is used for storing and displaying the images, the digitized intensities are preferably not converted back into an analog signal until the moment the representative summed intensities are displayed by the imaging means.

The X-ray line detectors used in the multiple detector scanner are each similar to the single X-ray line detector 22 shown in FIGS. 1 and 2. However, in a dual detector system. It is preferred to construct each scintillator crystal of each of the detectors 39 and 41 in FIGS. 3 and 4 with a square cross section. The square cross sections permit the pair of pencil beams 38 and 40, or pencil beams 49 and 50, to be as close as possible; the closer the pair of pencil beams are to each other, the fewer linear array memories required for a given scan speed and given translation motion speed.

Figure 5:
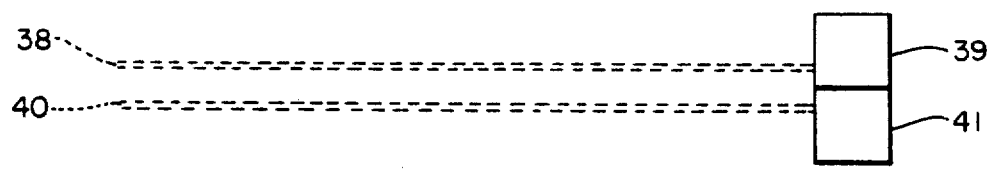
FIG. 5 is a diagrammatic representation of the cross section of the side-by-side detectors shown in FIGS. 3 and 4.

Referring now to FIG. 5, there is shown a diagrammatic representation of the cross section of the detectors 39 and 41. In a specific embodiment of the invention, the scintillator crystal for each detector is NaI(T1) with a cross section of 1.5 inches by 1.5 inches and 32 inches long. The total separation between the two crystals is 1/16 inch, and they are optically isolated. This configuration allows the two pencil beams 38 and 40 to be closer to each other at the detectors than the two crystals' center-to-center distance of 1 9/16 inches; the actual pencil beam separation used in the specific embodiment is approximately ⅜ inch; crystals made at the dimensions of ¼ inch × ¼ inch × 32 inches are preferably not used because of the large light attenuation for such a small cross section over the length of 32 inches. The ratio of the square root of cross section area to length is thus greater than 1/64 and preferably of the order of 3/64.

Figure 6:
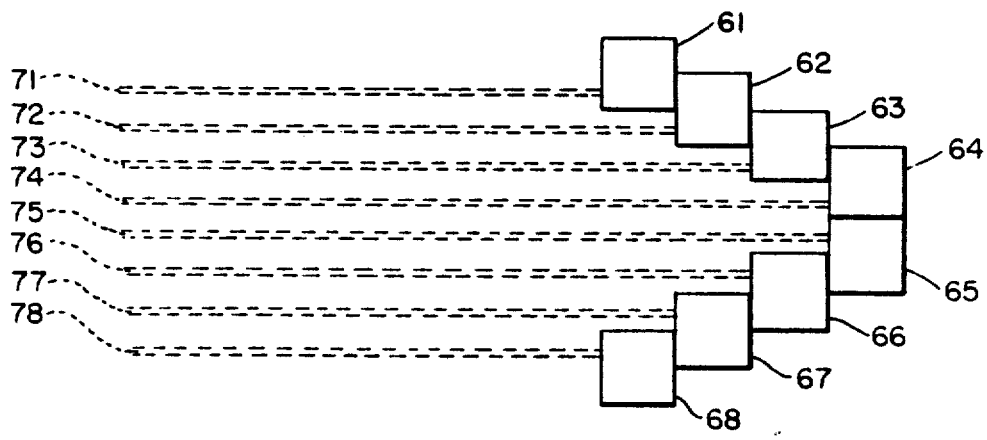
FIG. 6 is a diagrammatic representation of the cross section of a multiple detector system using more than two detectors in a stepped configuration.

Referring now to FIG. 6, there is shown a diagrammatic representation of the cross section of a multiple detector system using more than two detectors. In this staircase configuration the long crystal detectors 61, 62, 63, 64, 65, 66, 67, and 68, each of a particular dimension, such as 1.5 inches by 1.5 inches by 32 inches long may be arranged in the manner shown such that the multiple series of X-ray pencil beams 71, 72, 73, 74, 75, 76, 77, and 78 may scan the entire 32 inch length of the multiple detector with equal spacings, as close as is feasible, and the detector outputs for corresponding points of the object being scanned cumulatively combined to further enhance density contrast. It is also clear that any number of detectors may be used in this arrangement to further enhance density contrast.

The specific means for adding intensities is not a part of this invention and many techniques may be practiced by those skilled in the art. Thus, computer memories may store digitized representations of the density signal for an object provided by each detector, and the computer may add the representations for each point to provide a sum signal for each point that may be visually displayed. While digital techniques are preferred, analog techniques may be used. For example, video output signals from the different detectors may be applied to respective video storage tubes which may then be scanned to provide a number of stored video signals that are added together to provide a combined video signal which enhanced density contrast.

There has been described a novel X-ray imaging system characterized by selectively variable resolution, contrast and magnification, simple operation by relatively unskilled operators, and numerous other features. It is evident that those skilled in the art may now make numerous uses and modifications of and departures from the specific embodiments described herein without departing from the inventive concepts. For example, the disclosure herein has been in terms of pencil beams scanning straight lines at the interception of the pencil beam and a plane-in-space representing the displayed image. However, it is also within the scope of the invention to scan curved lines, rather than straight lines. Consequently, the invention is to be construed as embracing each and every novel feature and novel combination of features present in or possessed by the apparatus and techniques herein disclosed and limited solely by the spirit and scope of the appended claims.

What is claimed is:

1. A radiant energy image scanner which is capable of adjusting a characteristic of an image produced thereby, said scanner comprising:

a source of penetrating radiant energy, scanning means responsive to said source of penetrating radiant energy for producing at least one scanning pencil beam of penetrating radiant energy, radiant energy detector means scanned by said at least one scanning pencil beam to provide an image signal, display means responsive to said image signal for producing an image representative of the radiant energy response of a region scanned by said pencil beam, in which said scanning means includes, a first rotating energy opaque member intercepted by energy from said source of penetrating radiant energy with at least two sets of energy transparent areas thereon, a first set of areas each of area $A_1$ and number $N_1$ and a second set of areas each of area $A_2$ and number $N_2$, wherein at least one of $A_1$ or $N_1$ is not equal to $A_2$ or $N_2$, respectively, a second energy opaque member intercepted by energy from said source of penetrating radiant energy with at least two energy transparent areas thereon, and selection means for relatively positioning said first and second members to align a selected area of said second member with different ones of areas of one of said sets of areas of said first member and said source of penetrating radiant energy as said first member rotates.

2. The apparatus of claim 1 wherein said first member rotates about an axis and wherein said first set of energy transparent areas are equally spaced about said axis at radial distance $R_1$ and said second set of energy transparent areas are equally spaced about said axis at a different radial distance $R_2$, and wherein said second member includes an energy transparent area for each of said sets of areas of said first member, each said area having a dimensions selected so that when said first and second members are positioned by said selection means, penetrating radiant energy is transmitted by only one energy transparent area of said first member at any time.

3. The apparatus of claim 1 wherein said source of penetrating radiant energy comprises an X-ray source.

4. The apparatus of claim 3 in which said first rotating member has at least two sets of energy transparent areas, each area of a set having identical surface area and with surface area different from the surface area of areas of a different set of energy transparent areas.

5. The apparatus of claim 3 in which said first rotating member has at least two sets of energy transparent areas with a number of such areas in one set diferent from the number of such areas in another set.

6. The apparatus of claim 3 in which said first rotating member is in the form of a disc with sets of energy transparent areas at different radial positions from an axis of revolution.

7. The apparatus of claim 6 in which said second member is planar and positioned between said source and said first rotating member, and in which a first of said at least two energy transparent areas has a dimension different from a corresponding dimension of another of said at least two energy transparent areas.

8. The apparatus of claim 3 in which said first rotating member is a drum with energy transparent areas on a cylindrical surface of said drum with different sets of energy transparent areas distributed at different lengths along said cylindrical surface from a common datum, and different areas within a set distributed about the periphery of said cylindrical surface.

9. The apparatus of claim 8 in which said second member is planar and positioned with said first rotating member between said second member and said source.

10. The apparatus of claim 8 which further includes a collimator of triangular cross-section positioned between said source and said first rotating member for directing a fan beam of said radiant energy onto said cylindrical surface.

11. Improved radiant energy imaging apparatus of the type having a source of penetrating radiant energy, radiant energy detecting means, means for shaping said radiant energy into a pencil beam and for scanning with said pencil beam along said radiant energy detecting means to provide an image signal, means for relatively displacing the region traversed by said pencil beam and an assembly comprising said source and said detecting means to produce a sequence of image signals for producing an image representative of the radiant energy response of said region, wherein the improvement comprises an imaging apparatus capable of altering a characteristic of sid image in which said:

means for shaping and scanning comprises a first radiant energy opaque member with at least two displaced sets of energy transparent slits, at least a first set of slits of number $N_1$ each of area $A_1$ and a second set of slits of number $N_2$ each of area $A_2$, wherein at least one of $A_1$ or $N_1$ is not equal to $A_2$ or $N_2$, respectively, said first radiant energy opaque member rotating about an axis and located to intercept said radiant energy, and a second energy opaque member with at least two energy transparent slits also located to intercept said radiant energy, and means for altering a characteristic of said image by relatively displacing said axis and said second member whereby said energy is intercepted by slits of one or another of said sets of slits as said first member rotates.

12. The apparatus of claim 11 wherein
said first set of slits of said first member are equally spaced at a radial distance $R_1$ from said axis and said second set of slits of said first member are equally spaced at a different radial distance $R_2$ from said axis, and
wherein said second member has an energy transparent slit for each of said sets of slits, each slit of said second member of dimension to ensure that, when said axis and second member are displaced, penetrating radiant energy passes only one slit of said first member at any time.

13. The apparatus of claim 11 in which said first member comprises a disc with at least two sets of slits, said sets of slits located at different radial distances from said axis.

14. The apparatus of claim 11 in which said source of penetrating radiant energy is an X-ray source and said second energy opaque member is located between said X-ray source and said disc.

15. The apparatus of claim 13 in which the first set of slits has more slits than the slits in said second set of slits, and each of said slits of said first set is wider than slits in said second set.

16. The apparatus of claim 11 in which said first member comprises a drum, with at least two sets of slits, said sets of slits located circumferentially at different longitudinal distances from a common datum of said drum.

17. The apparatus of claim 16 in which said source of penetrating radiant energy comprises a source of X-rays, and collimator means producing a fan beam of X-rays, said collimator means with an entrance end adjacent said source of X-rays and and exit located within said drum.

18. The apparatus of claim 17 wherein said second member includes at least one slit for each of said sets of slits of said first member and is located between said drum and said detector.

19. The apparatus of claim 16 in which a first set of slits includes more slits than included within said second set, and each of said slits in said first set is wider than the slits in said second set.

20. The apparatus of claim 11 which includes display means for displaying the image produced with either a first or second set of slits, said image displayed within the same area to provide magnification of one image relative to another.

21. The apparatus of claim 11 wherein said source of penetrating radiant energy comprises an X-ray source,
and wherein said detecting means comprises means for converting incident X-ray energy into light energy, and
photodetecting means responsive to said light energy for providing an electrical image signal that is representative of the instantaneous radiant energy incident upon said detecting means.

22. The apparatus of claim 21 wherein said detecting means is a crystal from the group consisting of sodium iodide, cesium iodide and bismuth germanate, and said photodetecting means is adjacent to said crystal.

* * * * *